US006323384B1

United States Patent
Powers et al.

(10) Patent No.: US 6,323,384 B1
(45) Date of Patent: *Nov. 27, 2001

(54) PROCESS FOR ISOMERIZING LINEAR OLEFINS TO ISOOLEFINS

(75) Inventors: Donald H. Powers, Humble; Brendan D. Murray; Bruce H. C. Winquist, both of Houston, all of TX (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/711,044

(22) Filed: Jun. 5, 1991

(51) Int. Cl.$^7$ .............................. C07C 5/22; C07C 5/27; B01J 29/06
(52) U.S. Cl. ............................................. 585/671; 502/64
(58) Field of Search ............................... 585/671; 502/64

(56) References Cited

U.S. PATENT DOCUMENTS

| | | | |
|---|---|---|---|
| 2,217,252 | 10/1940 | Hoog | 260/683 |
| 3,558,733 | 1/1971 | Myers | 260/683.2 |
| 3,763,261 | 10/1973 | Sobel | 260/683.49 |
| 3,864,283 | 2/1975 | Schutt | 252/455 Z |
| 3,992,466 | 11/1976 | Plank et al. | 260/671 |
| 4,000,248 | 12/1976 | Martin | 423/329 |
| 4,016,245 | 4/1977 | Plank et al. | 423/328 |
| 4,038,337 | 7/1977 | Manara et al. | 260/683.2 |
| 4,046,859 | 9/1977 | Plank et al. | 423/328 |
| 4,146,584 | 3/1979 | Rollman | 260/673 |
| 4,150,062 | 4/1979 | Garwood et al. | 260/673 |
| 4,251,499 | 2/1981 | Nanne et al. | 423/329 |
| 4,324,940 | 4/1982 | Dessau | 585/466 |
| 4,330,679 * | 5/1982 | Kohler et al. | 502/159 |
| 4,343,692 | 8/1982 | Winquist | 208/111 |
| 4,377,502 | 3/1983 | Klotz | 252/455 Z |
| 4,405,500 | 9/1983 | Muller et al. | 252/433 |
| 4,503,282 | 3/1985 | Sikkenga | 585/671 |
| 4,548,913 | 10/1985 | Schwerdtel et al. | 502/68 |
| 4,584,286 | 4/1986 | Valyocsik | 502/62 |
| 4,721,607 | 1/1988 | Haddad et al. | 423/277 |
| 4,727,203 * | 2/1988 | Hamilton, Jr. | 585/670 |
| 4,749,819 | 6/1988 | Hamilton, Jr. | 585/329 |
| 4,777,322 | 10/1988 | Hoelderich et al. | 585/666 |
| 4,783,555 | 11/1988 | Atkins | 568/695 |
| 4,804,802 | 2/1989 | Evans et al. | 585/734 |
| 4,814,519 | 3/1989 | Harandi et al. | 568/697 |
| 4,886,934 | 12/1989 | Maxwell et al. | 585/660 |
| 4,922,048 | 5/1990 | Harandi . | |
| 4,942,027 | 7/1990 | Evans | 423/328 |
| 4,982,046 | 1/1991 | Guth | 585/533 |
| 5,091,590 | 2/1992 | Harandi et al. | 568/697 |
| 5,132,467 | 7/1992 | Haag et al. . | |
| 5,243,090 * | 9/1993 | Haag et al. | 568/697 |

FOREIGN PATENT DOCUMENTS

| | | | | |
|---|---|---|---|---|
| 0012473 | 6/1980 | (EP) | | C01B/33/28 |
| 0026041 | 4/1981 | (EP) | | C07C/41/06 |
| WO 91/18851 | 12/1991 | (WO) | | C07C/11/09 |

OTHER PUBLICATIONS

GB 8612815, for "Restructuring of Olefins," filed May 27, 1986, abandoned: (Certificate–2 pp, Request for Grant–2 pp, and specification–24 pp).
Catalytic Processes And Proven Catalysts, Charles L. Thomas, Academic Press, 1970, Chapter 3. "Isomerization".
P. Grandvallet and J. Suurd, Confidential Report AMGR.89.140, selected pages, Shell Internationale Research Maatschappij B. V.
Pujado, "Industrial Catalytic Applications of Molecular Sieves," *Catalysts Today* 13:113–141 (1992).
Catalytic Cracking and Skeletal Isomerization of n–Hexene on ZSM–5, J. Abbot and B. W. Wojciechowski, Canadian Journal of Chemical Engineering, vol. 63, Jun. 1985, pp. 451–61.

* cited by examiner

Primary Examiner—Jyothsna Venkat
Assistant Examiner—Maurie E. Garcia
(74) Attorney, Agent, or Firm—Tim L. Burgess

(57) ABSTRACT

This invention provides a process to convert linear alkenes such as butene-1 and butene-2 to methyl branched chain alkenes such as isobutylene using the hydrogen form of ferrierite. The hydrogen form of ferrierite has a pore size which allows the branched chain alkenes to form and diffuse out of the catalyst while reducing the formation of unwanted by-products, including dimers, trimers, aromatics and coke. This invention has been demonstrated with H-ferrierite in a laboratory scale reactor. Selectivities approaching 100% were demonstrated for isobutylene formation using H-ferrierite.

72 Claims, 3 Drawing Sheets

PROCESS FOR ISOMERIZING LINEAR OLEFINS TO ISOOLEFINS

FIELD OF THE INVENTION

This invention relates to structural isomerization of linear olefins to isoolefins using zeolite compositions as isomerizing catalysts.

BACKGROUND OF THE INVENTION

Increasing demand for high octane gasoline blended with lower aliphatic alkyl ethers such as octane boosters and supplementary fuels has created a significant demand for isoalkylethers, especially the $C_5$ to $C_7$ methyl, ethyl and isopropyl-t-alkyl ethers. Consequently, there is an increasing demand for the corresponding isoalkene starting materials such as isobutene, isoamylenes and isohexenes.

In many instances, it is desirable to convert an alkene such as normal butene, to a methyl branched alkene, for example isobutylene, by mechanisms such as structural isomerization. Such converted isoalkenes then can be reacted further, such as by polymerization or oxidation, to form useful products. Normal alkenes containing four carbon atoms (1-butene, trans-2-butene and cis-2-butene) and five carbon atoms (1-pentene, trans-2-pentene, and cis-2-pentene) are relatively inexpensive starting compounds. Conventionally, butenes and amylenes, including to a minor extent isobutylene and isoamylene, are obtained as a by-product from refinery and petrochemical processes such as catalytic and thermal cracking units.

Zeolite materials, both natural and synthetic, are known to have catalytic properties for many hydrocarbon processes. Zeolites typically are ordered porous crystalline aluminosilicates having a definite structure with cavities interconnected by channels. The cavities and channels throughout the crystalline material generally can be of such a size to allow selective separation of hydrocarbons. Such a hydrocarbon separation by the crystalline aluminosilicates essentially depends on discrimination between molecular dimensions. Consequently, these materials in many instances are known in the art as "molecular sieves" and are used, in addition to catalytic properties, for certain selective adsorptive processes. Zeolite molecular sieves are discussed in great detail in D. W. Breck, *Zeolite Molecular Sieves,* Robert E. Krieger Publishing Company, Malabar, Fla. (1984)

Generally, the term "zeolite" includes a wide variety of both natural and synthetic positive ion-containing crystalline aluminosilicate materials, including molecular sieves. They generally are characterized as crystalline aluminosilicates which comprise networks of $SiO_4$ and $AlO_4$ tetrahedra in which silicon and aluminum atoms are cross-linked in a three-dimensional framework by sharing of oxygen atoms. This framework structure contains channels or interconnected voids that are occupied by cations, such as sodium, potassium, ammonium, hydrogen, magnesium, calcium, and water molecules. The water may be removed reversibly, such as by heating, which leaves a crystalline host structure available for catalytic activity. The term "zeolite" in this specification is not limited to crystalline aluminosilicates. The term as used herein also includes silicoaluminophosphates (SAPO), metal integrated aluminophosphates (MeAPO and ELAPO), metal integrated silicoaluminophosphates (MeAPSO and ELAPSO). The MeAPO, MeAPSO, ELAPO, and ELAPSO families have additional elements included in their framework. For example, Me represents the elements Co, Fe, Mg, Mn, or Zn, and El represents the elements Li, Be, Ga, Ge, As, or Ti. An alternative definition would be "zeolitic type molecular sieve" to encompass the materials useful for this invention.

Developments in the art have resulted in formation of many synthetic zeolitic crystalline materials. Crystalline aluminosilicates are the most prevalent and, as described in the patent literature and in the published journals, are designated by letters or other convenient symbols. Zeolites have been specifically named and described as Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite ZSM-23 (U.S. Pat. No. 4,076,842), Zeolite ZSM-35 (U.S. Pat. No. 4,016,245), Zeolite ZSM-48 (U.S. Pat. No. 4,375,573), Zeolite NU-1 (U.S. Pat. No. 4,060,590) and others. Various ferrierite zeolites, including the hydrogen form of ferrierite, are described in U.S. Pat. Nos. 3,933,974, 4,000,248 and 4,942,007 and patents cited therein. SAPO-type catalysts are described in U.S. Pat. No. 4,440,871. MeAPO type catalysts are described in U.S. Pat. Nos. 4,544,143 and 4,567,029; ELAPO catalysts are described in U.S. Pat. No. 4,500,651, and ELAPSO catalysts are described in European Patent Application 159,624.

Up until now, catalysts for structurally isomerizing alkenes, particularly butene to isobutene, have utilized large pore zeolites having two or three-dimensional interconnecting channels, together with an associated catalytic metal such as platinum, palladium, boron or gallium. Continuing problems with present methods using such zeolites are coking of the catalyst pore spaces and undesirable by-product formation, in particular dimers, trimers and aromatics.

SUMMARY OF THE INVENTION

In the methods of this invention, a linear olefin is converted under isomerizing conditions to a methyl branched olefin using an isomerizing catalyst composition made up of a zeolite having only in one dimension a pore structure having a pore size small enough to retard by-products and retard the formation of coke and its precursors and large enough to permit entry of the linear olefin and diffusion of the isoolefin product. Generally, zeolites having in one dimension a pore structure with a pore size ranging from more than about 0.42 nm to less than about 0.7 nm are useful for the processes of this invention. Zeolites with this specified pore size are typically referred to as medium or intermediate pore zeolites and typically have a 10-member (or puckered 12-member) ring channel structure in one dimension and an 8-member or less (small pore) in the other dimensions, if any. For purposes of this invention, a one-dimensional pore structure is considered one in which the channels having the desired pore size do not interconnect with other channels of similar or larger dimensions; it may also be considered alternatively as a channel pore structure (see U.S. Pat. No. 3,864,283) or uni-directional sieve. Such one-dimensional, intermediate pore size catalyst compositions provide increased selectivity of the isomerization reaction, decreased dimer and trimer by-product formation, and decreased coking of the catalyst.

Zeolites that contain small pores (i.e., less than about 0.42 nm) do not allow for diffusion of the methyl branched isoolefin product, e.g., isobutylene; while zeolites that contain large pores (i.e., greater than about 0.7 nm) in any one dimension are subject to substantial by-product formation and coking. Coking is believed to be the result of oligomerization and polymerization, aromatization, or alkylation of the feed paraffin or olefin hydrocarbons. Zeolites of this invention should contain at least one pore dimension with the specified pore size. A two or three-dimensional pore structure having the specified pore size would permit substantial contact of the isomerizing olefins and thereby facilitate unwanted dimerization and trimerization reactions.

The processes of this invention are characterized by selectivities which range from about 70% to 99% over run lengths of 48 to 120 hours, and isoolefin yields of between about 30% to 37% at the beginning of a run and 12% to 20% at the end of run conditions.

DETAILED DESCRIPTION OF THE PREFERRED EMBODIMENTS

Hydrocarbon Feed Stream

Figure 1:
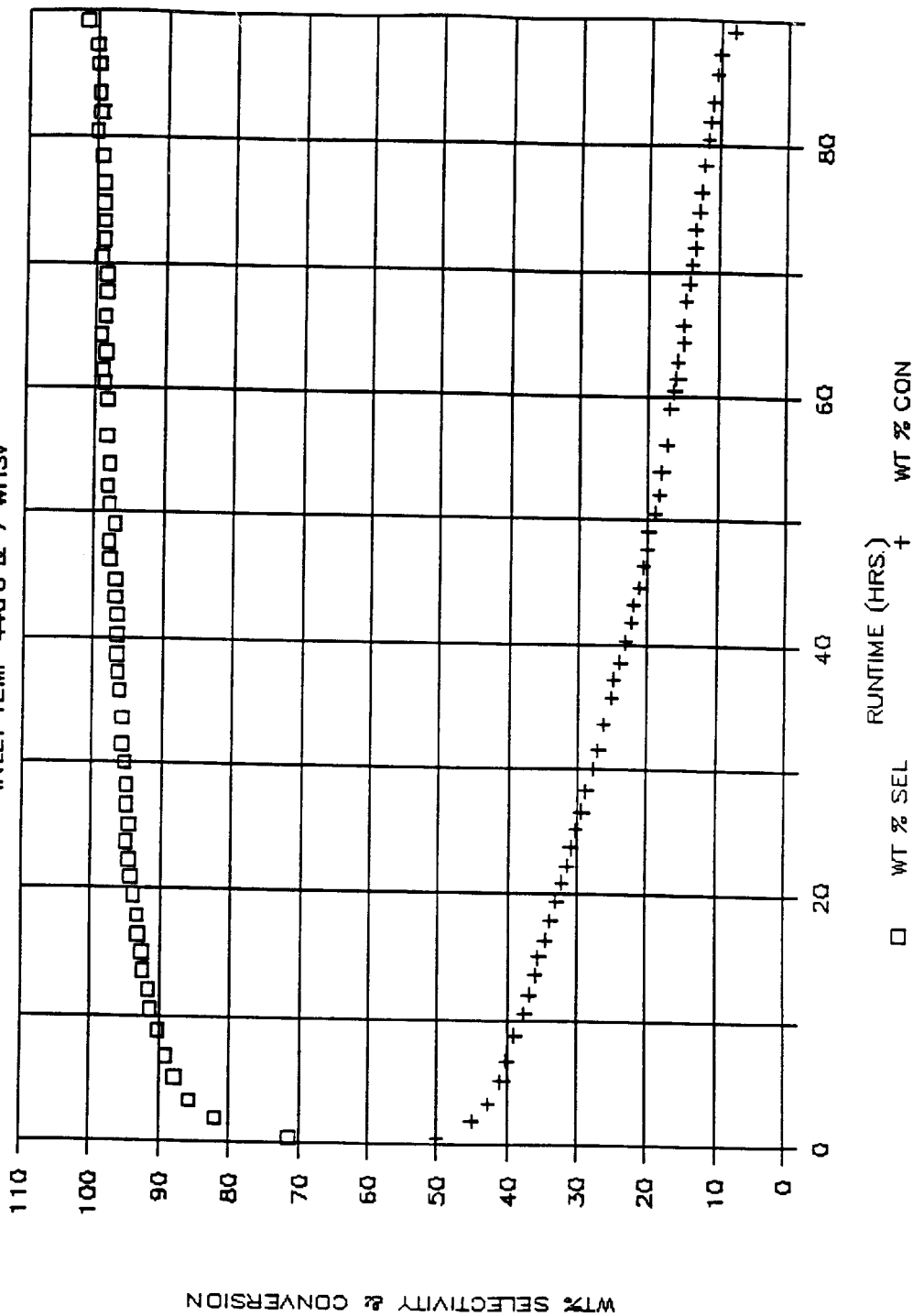
FIG. 1 is a graph of conversion and selectively versus run time illustrative of a process of this invention.

The hydrocarbon feed useful for this invention comprises a substantially linear alkene. Typically, the linear alkene will contain four to ten carbon atoms. Also considered a linear alkene for purposes of this invention is a compound containing a linear alkene segment with four to ten carbon atoms. It is believed that long chain linear alkenes and compounds containing long chain linear segments may penetrate the zeolite catalyst for a distance effective to allow isomerization. Thus, the entire molecule need not be small enough to fit entirely within the pore structure of the catalyst. The preferred feed contains butylene or amylene.

As used herein, n-butylene includes all forms of n-butylene, for example 1-butene and 2-butene, either trans-2-butene or cis-2-butene, and mixtures thereof. As used herein, n-amylene or n-pentene, includes 1-pentene, cis- or trans-2-pentene, or mixtures thereof. The n-butylene or n-amylene used in the processes of this invention is generally in the presence of other substances such as other hydrocarbons. Thus, a feedstream used in the process of the invention containing n-butylene or n-amylene also can contain other hydrocarbons such as alkanes, other olefins, aromatics, hydrogen, and inert gases. Typically, the n-butene feedstream used in this invention contains about 40 to about 100 wt. % n-butene. For example, a hydrocarbon feedstream from a fluid catalytic cracking effluent stream generally contains about 40 to about 60 wt. % normal butene and a hydrocarbon effluent from an ether processing unit, such as a methyl-tert-butyl ether (MTBE) processing unit generally containing from 40 to about 100 wt. % n-butylene.

As used herein, the term "alkene" can be alternatively referred to as "olefin"; the term "linear" can be alternatively referred to as "normal"; and the term "isoolefin" can be alternatively referred to as "methyl branched isoolefin." Similarly, butene and butylene refer to the same four carbon alkene; and pentene and amylene refer to the same five carbon alkene.

Isomerizing Catalyst

The zeolite catalyst useful in the processes of this invention comprises a zeolite having one-dimensional pore structures with a pore size ranging from greater than about 0.42 nm and less than about 0.7 nm. The zeolite catalyst preferably comprises substantially only zeolites with the specified pore size in one dimension. Zeolites having pore sizes greater than 0.7 nm are susceptible to unwanted aromatization, oligimerization, alkylation, coking and by-product formation. Further, two or three-dimensional zeolites having a pore size greater than 0.42 nm in two or more dimensions permit dimerization and trimerization of the alkene. Hence, zeolites having a pore diameter bigger than about 0.7 nm in any dimension or having a two or three-dimensional pore structure in which any two of the dimensions has a pore size greater than about 0.42 nm are excluded as part of this invention.

Examples of zeolites that can be used in the processes of this invention, which have one-dimensional pore structures with a pore size between about 0.42 nm and 0.7 nm, include the hydrogen form of ferrierite, SAPO-11, SAPO-31, SAPO-41, FU-9, NU-23, NU-10, ZSM-12, ZSM-22, ZSM-23, ZSM-35, ZSM-48, ZSM-50, MeAPO-11, MeAPO-31, MeAPO-41, MeAPSO- 11, MeAPSO 31, and MeAPSO-41, ELAPO-11, ELAPO-31, ELAPO-41, ELAPSO-11, ELAPSO-31, and ELAPSO-41, laumontite, clinoptilolite, cancrinite, offretite, hydrogen form of heulindite, hydrogen form of stilbite, and the magnesium or calcium form of mordenite. The isotypic structures of these frameworks, known under other names, are considered to be equivalent. An overview describing the framework compositions of many of these zeolites is provided in *New Developments in Zeolite Science Technology*, "Aluminophosphate Molecular Sieves and the Periodic Table," Hanigen et al. (Kodansha Ltd., Tokyo, Japan 1986).

Many natural zeolites such as ferrierite, heulindite and stilbite feature a one-dimensional pore structure with a pore size slightly smaller than the desired 0.42 nm diameter. These same zeolites can be converted to zeolites with larger pore sizes by removing the associated alkali metal or alkaline earth metal by methods known in the art, such as ammonium ion exchange, optionally followed by calcination, to yield the zeolite in its hydrogen form. See e.g., U.S. Pat. Nos. 4,795,623 and 4,942,027 incorporated herein by reference. Replacing the associated alkali or alkaline earth metal with the hydrogen form correspondingly enlarges the pore diameter. It is understood that the pore diameter or "size" shall mean the effective pore diameter or size for diffusion. Alternatively, natural zeolites with too large a pore size, such as mordenite, can be altered by substituting the alkali metal with larger ions, such as alkaline earth metals to reduce the pore size and thus become useful for the processes of this invention.

Exemplary of zeolites that are not useful for the processes of this invention include ZSM-5, erionite, zeolite Y, hydrogen form of mordenite, and faujasite.

The zeolite catalyst used in the isomerization processes of this invention can be used alone or suitably combined with a refractory oxide that serves as a binder material. Suitable refractory oxides include natural clays, such as bentonite, montmorillonite, attapulgite, and kaolin; alumina; silica; silica-alumina; hydrated alumina; titania; zirconia and mixtures thereof. The weight ratio of binder material and zeolite suitably ranges from 1:9.5 to 9:1, preferably 1:4.

Catalytic compositions comprising the crystalline zeolite material of the invention and a suitable binder material can be formed by blending a finely divided crystalline zeolite with a binder material. The resulting mixture is thoroughly blended and mulled typically by adding water and/or a volatizable acidic material such as nitric acid or acetic acid.

The resulting gel can be dried and calcined, for example, at temperatures between about 450° C. and 550° C., preferably between about 500° C. and 520° C., to form a composition in which the crystalline zeolite is distributed throughout the matrix of binder material. Additionally, the catalyst composition can be extruded to form pellets, cylinders, or rings, or shaped into spheres, wagon wheels or polylobe structures.

H-Ferrierite Catalyst

A hydrogen exchanged ferrierite with a molar silica ($SiO_2$) to alumina ($Al_2O_3$) ratio of about 18, a sodium content less than 0.01 wt. % and a surface area of 420 square meters/gram was used to prepare the catalyst. The framework of this zeolite contained both 8 and 10 T-atom rings arranged as described on pages 64 and 65, of the book "Atlas of Zeolite Structure Types" by W. M. Meier and D. H. Olson, Butterworths, 2nd Edition, 1987. The pore dimensions of the 8 and 10 T-atom rings in this H-ferrierite are slightly larger than 3.5 Å×4.8 Å and 4.2 Å×5.4 Å, respectively. Not including the microporosity of the zeolite, the finished catalyst pore size distribution by mercury intrusion was bi-modal in nature with peaks at approximately 35 and 1150 angstroms. This material was extruded with alumina and calcined at 500° C. to produce 1/16" cylinders of a H-ferrierite catalyst with the following measured physical properties.

| | |
|---|---|
| Loss On Ignition @ 1100° C. | 6.7 wt % |
| $SiO_2$ (anhydrous w/o binder) | 91.7 wt % |
| $Al_2O_3$ (anhydrous w/o binder) | 8.5 wt % |
| $Na_2O$ | 0.01 wt % |
| CaO | 0.01 wt % |
| MgO | 0.01 wt % |
| $Fe_2O_3$ | 0.05 wt % |
| Compacted Bulk Density (finished catalyst) | 40 lb/ft$^3$ |
| Surface Area (zeolite powder, P/Po) | 420 m$^2$/gram |
| Surface Area (finished catalyst) | 376 m$^2$/gram |
| Binder | 20 wt % |

H-ferrierite is the preferred zeolite catalyst for use in the isomerization processes of this invention. H-ferrierite is derived from ferrierite, a naturally occurring zeolite mineral having a composition varying somewhat with the particular source. A typical elemental composition of ferrierite is

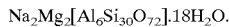

$Na_2Mg_2[Al_6Si_{30}O_{72}] \cdot 18H_2O$.

The prominent structural features of ferrierite found by x-ray crystallography are parallel channels in the aluminosilicate framework. These channels, which are roughly elliptical in cross-section, are of two sizes: larger channels having major and minor axes of 5.4 and 4.2 Å, respectively, and smaller parallel channels having major and minor axes of 4.8 and 3.5 Å, respectively. Conversion of ferrierite to its hydrogen form, H-ferrierite, replaces sodium cations with hydrogen ions in the crystal structure. Both the alkali metal and hydrogen forms reject multiple branched chain and cyclic hydrocarbon molecules and retard coke formation. According to the purposes of this invention, H-ferrierite is considered to be comprised substantially of a one-dimensional pore structure having an elliptical pore size (>0.54 nm and >0.42 nm) large enough to permit entry of the linear olefin and diffusion of the methyl branched isoolefin and small enough to retard coke formation. The one-dimensional feature is satisfied because there are no other interconnecting channels which have diameters similar to or greater than the primary (>0.54 nm and >0.42 nm) channel.

Various methods are provided which teach procedures for preparing H-ferrierite, including U.S. Pat. Nos. 4,795,623 and 4,942,027, incorporated herein by reference. In making the H-ferrierite, the H-ferrierite will typically have a silica ($SiO_2$):alumina ($Al_2O_3$) molar ratio of greater than about 5:1, suitably have a ratio of between 5:1 and 100:1, desirably have a ratio between about 5:1 and about 30:1 and preferably have a ratio of between about 5:1 and about 20:1.

Isomerizing Conditions

In the processes of this invention, a hydrocarbon stream comprising a linear olefin is contacted with the catalytic zeolite under isomerizing conditions. Generally, in the processes of this invention, the hydrocarbon stream is contacted with the above-described zeolite catalyst in a vapor phase at a suitable reaction temperature, pressure and space velocity. Generally, suitable reaction conditions include a temperature of about 250° C. to about 650° C., an olefin partial pressure of above about 0.5 atmosphere, and a total pressure of about 0.5 to about 10.0 atmospheres or higher, a hydrogen/hydrocarbon molar ratio of 0 to about 30 or higher, substantially free of water (i.e., less than about 2.0 wt % of the feed), and a hydrocarbon weight hourly space velocity (WHSV) of about 1.0 to about 50 hr$^{-1}$. The hydrogen can be added directly to the feed stream prior to introduction of the isomerization zone, or the hydrogen can be added directly to the isomerization zone. In a typical process scheme, an olefin-containing hydrocarbon vapor stream is contacted with such catalyst in a reactor at about 300° C. to about 475° C., at an olefin partial pressure of about 10 psia to about 20 psia and a total pressure of about 15 to about 30 psia, without added hydrogen, and at a hydrocarbon based WHSV of about 2 to about 28 hr$^{-1}$. Preferred isomerizing conditions are carried out at a temperature of between about 400° C. to 440° C., at atmospheric pressures, and a hydrocarbon based WHSV of between about 7 to about 15 hr$^{-1}$.

The process according to the present invention can be carried out in a packed bed reactor, a fixed bed, fluidized bed reactor or a moving bed reactor. The bed of the catalyst can move upward or downward.

During the process, some coke will be formed on the catalyst. Therefore, it is advantageous to regenerate the catalyst. The catalyst can be regenerated by subjecting it to heat treatment with air, nitrogen/oxygen gas mixture, or hydrogen. A continuous regeneration, similar to the regeneration carried out in a fluidized catalytic cracking process may be useful.

The performance of the zeolite catalyst can be affected by controlling the water content in the catalyst. Water content of the catalyst can be adjusted by methods such as adding water to the feed or by directly adding water to the reactor. Calcination conditions will also affect the water content of the catalyst. These methods are referred to as controlled hydration of the catalyst.

Description of the Testing Apparatus

The laboratory pilot unit was a semi-automated unit that can control flow, temperature, and pressure. It can also collect samples for analysis and record process variable data. The process variable data was collected with an analog to digital (A to D) input/output converter. The A to D converter was connected to a personal computer (PC) which runs a process control software package. This software package allowed the operator to monitor the process variable data and control the unit using proportional/integral/derivative (PID) control blocks for flow and pressure. It also archived the process variable data on magnetic media.

The pilot reactor occupied three separate hoods: The feed hood contained the feed system where the feed was stored in a five-gallon cylinder. The feed tank rested on a load cell that was used to monitor the weight of the feed cylinder. The feed tank was pressurized with a 60–80 psig nitrogen blanket. This nitrogen pressure fed the hydrocarbon feed containing butylenes to the system. The feed flow rate was controlled by PID control block in the process control software. This control block consisted of two flow meters, an instrument to pneumatic signal converter, and a flow control valve located downstream of the flow meters. The two flow meters were used independently and were calibrated for different flow rate ranges. The feed system also had an additional connection for bottled gas addition or water injection with the feed.

The reactor hood contained the reactor and heating furnace. The reactor was a 2 inch o.d. and 1.6 inch i.d. stainless steel pipe with 2-inch flanges welded to each end. The pipe also had ¼ inch feed and effluent lines welded on 6 inches from the bottom and top of the reactor respectively. The top sealing flange was fitted with a pressure gauge and rupture disk. The bottom sealing flange had a thermocouple well welded directly in the center of the flange that extends up through the middle of the reactor pipe when attached. The thermocouple well was a ½ inch stainless steel tube welded shut at one end and contained eight or more thermocouple points. The reactor pipe was enclosed with a Lindberg three foot heating furnace containing three heating zones but only the bottom zone was used to preheat the butylene feed to the reaction section. The furnace was controlled by three controllers comprising a PID control block for monitoring and controlling the temperature inside the reactor at each zone. Located on the effluent line was tubing and equipment for the sampling system. The sampling system included an air actuated valve and a steam traced line of helium that carried the sample to the gas chromatograph (GC) for direct injection.

The product hood contained the effluent cooler, the condensables collection tank, and the effluent pressure transmitter. The effluent condenser consisted of a coiled tube that contained the effluent line as the inner tube. Cooling water flowed through the outer tube to cool the effluent containing inner tube. Downstream of the condenser was the 5 gallon condensables collection tank. The effluent pressure was controlled by a PID control block in the process control software. This control block consisted of a pressure transducer (located upstream of the condenser), an instrument to pneumatic signal converter, and a pressure control valve (located downstream of the collection tank). A vent for the noncondensables was located downstream of the pressure valve.

Testing Procedure

The reactor was first loaded with an inert packing material in the preheating zone. The inert packing materials used were either a small mesh corundum or inert clay catalyst support balls. The inert bed depth varied depending on the thermocouple points the catalyst was to occupy. A typical loading depth was about 30 inches of inert material. Above the packing material a weighed amount of catalyst is added to coincide with thermocouple points for reading temperature during the experiment. The amount of catalyst used for the test varied depending on the weight hourly space velocity desired and the flow rates attainable with our equipment. A typical loading consisted of 97 grams of catalyst which corresponded to a loading of about 4 inches in the reactor. Above the catalyst another layer of packing material was added to form a distinct zone of catalyst.

Two different feed streams were used during the screening. One feed stream used was an MTBE processing effluent and comprised about 30–50% butene-2, 25–45% butene-1, and 20–30% n-butane. The other feed stream used for testing comprised about 90% butene-2 and 9% butene-1 (termed herein "butylenes feed").

Testing began by warming up the reactor to a minimum operating temperature usually greater than 200° C. The warming step was performed under a nitrogen purge of approximately 15–50 psia. Once the reactor was warmed, the flow control valve was opened to introduce feed to the reactor, and the nitrogen purge was turned off. WHSVs varied from 1 to 30 during the testing. The operating temperatures used for the testing varied in a range from 200° C. to 550° C. and depended on many factors, including the activity of the catalyst. The pressures used during the testing varied in response to restriction from the catalyst and reactor. Most all of the testing was performed with the pressure control valve open to the atmosphere. The recorded values of the effluent pressure, however, were in a range of about 15–45 psia.

Samples of the reactor effluent were manually sampled using the sampling system and gas chromatography. Sampling was performed manually rather than on an automatic specific time interval in order to have specific operating conditions for the process variables. The analysis was performed with a boiling point separation column or an alumina column.

Many different techniques were attempted to regenerate the catalysts. One technique was to burn the "coke" off the catalyst by putting a weighed amount in the muffle furnace at about 500° C. to 550° C. for approximately 12 hours. In situ catalyst regeneration was also successful. Both methods restored catalyst activity.

Calculations

Conversion and selectivity are calculated for each sample during testing runs and used for comparison of the various catalysts. It is believed that during the isomerization an equilibrium is achieved between butene-1 and trans and cis butene-2. Therefore the calculation of conversion and selectivity reflect the feed (FD) and effluent (EFF) concentrations of butene-1 (B1) and butene-2 (B2) and isobutylene (IB1). Conversion is calculated as:

$$\% \text{ Conversion} = \frac{(\text{wt}\% \ B1 + \text{wt}\% \ B2)FD - (\text{wt}\% \ B1 + \text{wt}\% \ B2)EFF}{(\text{wt}\% \ B1 + \text{wt}\% \ B2)FD} \times 100$$

selectivity is calculated as:

$$\% \text{ Selectivity} = \frac{(\text{wt}\% \ IB1)EFF - (\text{wt}\% \ IB1)FD}{(\text{wt}\% \ B1 + \text{wt}\% \ B2)FD - (\text{wt}\% \ B1 + \text{wt}\% \ B2)EFF} \times 100$$

and yield is calculated as $$\% \text{ Yield} = \frac{(\text{wt}\% \ IB1)Eff - (\text{wt}\% \ IB1)FD}{(\text{wt}\% \ B1 + \text{wt}\% \ B2)FD} \times 100$$

EXAMPLE 1

| CONDITIONS & COMPONENTS | FEED wt % | EFFLUENT @ 1 HOUR | EFFLUENT @ 5.6 HOURS | EFFLUENT @ 16 HOURS | EFFLUENT @ 36 HOURS |
|---|---|---|---|---|---|
| CATALYST: HYDROGEN FERRIERITE | | | | | |
| CATALYST CHARGE: 400 grams | | | | | |
| PRESSURE: 15–17 psia | | | | | |
| WHSV: 2 | | | | | |
| INLET TEMPERATURE | | 370° C. | 295° C. | 255° C. | 319° C. |
| METHANE | 0.00 | 0.08 | 0.00 | 0.00 | 0.00 |
| ETHANE | 0.01 | 0.13 | 0.01 | 0.01 | 0.01 |
| ETHYLENE | 1.17 | 0.20 | 0.17 | 0.33 | 0.25 |
| PROPANE | 0.00 | 3.14 | 0.08 | 0.03 | 0.10 |
| CYCLO PROPANE | 0.00 | 0.00 | 0.00 | 0.00 | 0.00 |
| PROPYLENE | 0.15 | 2.02 | 0.69 | 0.52 | 0.95 |
| ISO-BUTANE | 0.01 | 1.18 | 0.17 | 0.06 | 0.17 |
| N-BUTANE | 0.09 | 4.97 | 1.50 | 1.11 | 1.54 |
| METHYL CYC-PROPANE | 0.00 | 0.00 | 0.00 | 0.00 | 0.00 |
| TRANS 2-BUTENE | 57.67 | 3.46 | 10.95 | 20.17 | 10.43 |
| BUTENE-1 | 11.37 | 1.45 | 3.56 | 7.84 | 4.52 |
| ISOBUTYLENE | 0.02 | 7.69 | 16.10 | 12.57 | 19.50 |
| CIS 2-BUTENE | 29.45 | 2.38 | 7.45 | 14.21 | 7.17 |
| 1,3 BUTADIENE | 0.01 | 0.00 | 0.00 | 0.00 | 0.00 |
| HEAVIES (C5+) | 0.05 | 73.30 | 59.32 | 43.15 | 55.36 |

EXAMPLE 2

| CONDITIONS & COMPONENTS | FEED wt % | EFFLUENT @ 9 HOURS | EFFLUENT @ 21 HOURS | EFFLUENT @ 31 HOURS | EFFLUENT @ 49 HOURS |
|---|---|---|---|---|---|
| CATALYST: HYDROGEN FERRIERITE | | | | | |
| CATALYST CHARGE: 400 grams | | | | | |
| PRESSURE: 15–17 psia | | | | | |
| INLET TEMPERATURE | | 295° C. | 350° C. | 274° C. | 161° C. |
| WHSV | | 3 | 8 | 4 | 15 |
| METHANE | 0.00 | 0.00 | 0.01 | 0.00 | 0.07 |
| ETHANE | 0.01 | 0.01 | 0.02 | 0.01 | 0.12 |
| ETHYLENE | 1.17 | 0.22 | 0.28 | 0.46 | 0.84 |
| PROPANE | 0.00 | 0.07 | 0.15 | 0.03 | 0.64 |
| CYCLO PROPANE | 0.00 | 0.00 | 0.00 | 0.00 | 0.00 |
| PROPYLENE | 0.15 | 0.69 | 1.31 | 0.41 | 3.66 |
| ISO-BUTANE | 0.01 | 0.13 | 0.17 | 0.07 | 0.55 |
| N-BUTANE | 0.09 | 1.24 | 1.42 | 0.97 | 3.08 |
| METHYL CYC-PROPANE | 0.00 | 0.00 | 0.00 | 0.00 | 0.00 |
| TRANS 2-BUTENE | 57.67 | 12.49 | 9.74 | 23.13 | 18.58 |
| BUTENE-1 | 11.37 | 4.43 | 4.13 | 8.86 | 10.21 |
| ISOBUTYLENE | 0.02 | 14.83 | 17.94 | 11.29 | 26.95 |
| CIS 2-BUTENE | 29.45 | 8.65 | 6.89 | 15.72 | 13.69 |
| 1,3 BUTADIENE | 0.01 | 0.00 | 0.00 | 0.00 | 0.05 |
| HEAVIES (C5+) | 0.05 | 57.24 | 57.94 | 39.05 | 21.56 |

EXAMPLE 3

| CONDITIONS & COMPONENTS | FEED wt % | EFFLUENT @ 2 HOURS | EFFLUENT @ 12 HOURS | EFFLUENT @ 24 HOURS | EFFLUENT @ 31 HOURS | EFFLUENT @ 39 HOURS |
|---|---|---|---|---|---|---|
| CATALYST: HYDROGEN FERRIERITE | | | | | | |
| CATALYST CHARGE: 96 grams | | | | | | |
| PRESSURE: 15–17 psia | | | | | | |
| WHSV: 15 | | | | | | |
| INLET TEMPERATURE | | 251° C. | 319° C. | 371° C. | 372° C. | 371° C. |
| METHANE | 0.00 | 0.00 | 0.01 | 0.00 | 0.00 | 0.00 |
| ETHANE | 0.01 | 0.01 | 0.02 | 0.01 | 0.01 | 0.01 |
| ETHYLENE | 1.17 | 0.60 | 0.72 | 0.55 | 0.80 | 0.84 |
| PROPANE | 0.00 | 0.04 | 0.09 | 0.03 | 0.02 | 0.01 |
| CYCLO PROPANE | 0.00 | 0.00 | 0.00 | 0.00 | 0.00 | 0.00 |
| PROPYLENE | 0.15 | 0.19 | 1.25 | 0.81 | 0.70 | 0.57 |

-continued

| CONDITIONS & COMPONENTS | FEED wt % | EFFLUENT @ 2 HOURS | EFFLUENT @ 12 HOURS | EFFLUENT @ 24 HOURS | EFFLUENT @ 31 HOURS | EFFLUENT @ 39 HOURS |
|---|---|---|---|---|---|---|
| CATALYST: HYDROGEN FERRIERITE | | | | | | |
| CATALYST CHARGE: 96 grams | | | | | | |
| PRESSURE: 15–17 psia | | | | | | |
| WHSV: 15 | | | | | | |
| ISO-BUTANE | 0.01 | 0.02 | 0.12 | 0.06 | 0.03 | 0.02 |
| N-BUTANE | 0.09 | 0.47 | 1.22 | 0.86 | 0.72 | 0.55 |
| METHYL CYC-PROPANE | 0.00 | 0.00 | 0.00 | 0.01 | 0.04 | 0.02 |
| TRANS 2-BUTENE | 57.67 | 40.93 | 20.76 | 26.05 | 28.33 | 32.28 |
| BUTENE-1 | 11.37 | 17.60 | 9.59 | 13.95 | 14.14 | 16.47 |
| ISOBUTYLENE | 0.02 | 2.65 | 23.53 | 31.89 | 26.97 | 21.72 |
| CIS 2-BUTENE | 29.45 | 26.20 | 14.67 | 18.23 | 20.15 | 23.48 |
| 1,3 BUTADIENE | 0.01 | 0.00 | 0.00 | 0.00 | 0.00 | 0.00 |
| HEAVIES (C5+) | 0.05 | 11.29 | 28.02 | 7.55 | 8.09 | 4.03 |

EXAMPLE 4

The operating conditions for the next experimental run are as follows:

| CATALYST: | Hydrogen Ferrierite |
|---|---|
| FEED: | Butylenes |
| CATALYST WT.: | 97 grams |
| RUNTIME HOURS: | 180 hrs. |
| INLET TEMPS.: | 310°–420° C. |
| WHSVs: | 15 |
| PRESSURE: | 18 psia avg. |
| CONVERSION: | 26.6% |
| SELECTIVITY: | 70.1% |

For this experimental run, 97.7 grams of fresh catalyst was loaded in the reactor. During this experimental run hydrogen gas was added to the feed via the auxiliary feed line for 8–20 hours periodically over the 180 hour run time.

The hydrogen was added to the feed in an attempt to decrease "coking". The gasoline went from pale green to near water white in appearance in contrast to the pale green gasoline produced in runs without hydrogen.

EXAMPLE 5

For this experiment, a sample of "coked" hydrogen ferrierite was placed in the muffle furnace for about 12 hours at 500° C. in order to regenerate the catalyst by burning off the "coke". The catalyst returned from the regeneration with a white color similar to the original material. The catalyst sample was loaded into the reactor and charged with a butylene stream.

| CONDITIONS & COMPONENTS | FEED wt % | EFFLUENT @ 2 HOURS wt % | EFFLUENT @ 12 HOURS wt % | EFFLUENT @ 24 HOURS wt % | EFFLUENT @ 48 HOURS wt % | EFFLUENT @ 67 HOURS wt % |
|---|---|---|---|---|---|---|
| CATALYST: HYDROGEN FERRIERITE (REGENERATED) | | | | | | |
| CATALYST CHARGE: 97.70 grams | | | | | | |
| PRESSURE: 17–24 psia | | | | | | |
| WHSV: 15 | | | | | | |
| INLET TEMPERATURE (C.) | | 390° C. | 402° C. | 398° C. | 405° C. | 400° C. |
| METHANE | 0.00 | 0.02 | 0.01 | 0.00 | 0.03 | 0.00 |
| ETHANE | 0.01 | 0.04 | 0.01 | 0.01 | 0.00 | 0.01 |
| ETHYLENE | 0.86 | 0.07 | 0.63 | 0.67 | 0.02 | 0.87 |
| PROPANE | 0.00 | 0.00 | 0.00 | 0.00 | 0.01 | 0.01 |
| CYCLO PROPANE | 0.00 | 0.00 | 0.00 | 0.00 | 0.00 | 0.00 |
| PROPYLENE | 0.12 | 2.67 | 1.21 | 0.77 | 0.36 | 0.54 |
| ISO-BUTANE | 0.00 | 0.25 | 0.08 | 0.05 | 0.02 | 0.06 |
| N-BUTANE | 0.04 | 1.91 | 1.07 | 0.79 | 0.48 | 0.82 |
| METHYL CYC-PROPANE | 0.00 | 0.00 | 0.00 | 0.00 | 0.00 | 0.00 |
| TRANS 2-BUTENE | 57.88 | 18.75 | 24.12 | 27.83 | 32.56 | 36.09 |
| BUTENE-1 | 10.74 | 9.70 | 12.72 | 13.89 | 18.68 | 21.07 |
| ISOBUTYLENE | 0.00 | 34.14 | 34.70 | 30.62 | 21.05 | 12.73 |
| CIS 2-BUTENE | 30.26 | 13.78 | 17.46 | 20.02 | 23.84 | 25.99 |
| 1,3 BUTADIENE | 0.01 | 0.00 | 0.00 | 0.00 | 0.00 | 0.00 |
| HEAVIES (C5+) | 0.08 | 18.68 | 7.99 | 5.34 | 2.95 | 1.81 |

The following Examples 6–19 feature data illustrating isobutylene conversion using an MTBE processing effluent feed. The testing apparatus and procedure were the same as described above.

EXAMPLE 6

| COMPONENTS | CATALYST: HYDROGEN FERRIERITE<br>CATALYST CHARGE: 97.70 grams<br>PRESSURE: 17–18 psia<br>INLET TEMPERATURE: 390° C.<br>WHSV: 14 | | | | | | | |
|---|---|---|---|---|---|---|---|---|
| | INITIAL FEED wt % | INITIAL EFFLUENT wt % | FEED @ 12 HOURS wt % | EFFLUENT @ 12 HOURS wt % | FEED @ 24 HOURS wt % | EFFLUENT @ 24 HOURS wt % | FEED @ 48 HOURS wt % | EFFLUENT @ 48 HOURS wt % |
| METHANE | 0.08 | 0.06 | 0.08 | 0.05 | 0.01 | 0.01 | 0.01 | 0.00 |
| ETHANE | 0.00 | 0.02 | 0.00 | 0.00 | 0.00 | 0.00 | 0.00 | 0.00 |
| ETHYLENE | 0.00 | 0.05 | 0.00 | 0.01 | 0.00 | 0.01 | 0.00 | 0.00 |
| PROPANE | 0.00 | 0.06 | 0.00 | 0.00 | 0.00 | 0.00 | 0.00 | 0.00 |
| CYCLO PROPANE | 0.00 | 0.00 | 0.00 | 0.00 | 0.00 | 0.01 | 0.00 | 0.01 |
| PROPYLENE | 0.00 | 0.77 | 0.00 | 0.33 | 0.00 | 0.26 | 0.00 | 0.15 |
| ISO-BUTANE | 2.89 | 2.75 | 2.90 | 2.80 | 3.15 | 3.04 | 3.14 | 3.02 |
| N-BUTANE | 25.98 | 25.49 | 25.99 | 26.20 | 19.95 | 20.11 | 19.88 | 20.05 |
| METHYL CYC-PROPANE | 0.06 | 0.16 | 0.05 | 0.16 | 0.07 | 0.17 | 0.07 | 0.17 |
| TRANS 2-BUTENE | 24.38 | 18.16 | 24.39 | 21.54 | 16.54 | 25.00 | 16.46 | 28.09 |
| BUTENE-1 | 28.31 | 9.90 | 28.29 | 12.01 | 49.00 | 14.41 | 49.19 | 16.10 |
| ISOBUTYLENE | 0.24 | 20.66 | 0.23 | 17.64 | 0.26 | 15.77 | 0.25 | 10.61 |
| CIS 2-BUTENE | 17.90 | 13.12 | 17.88 | 15.32 | 10.78 | 18.16 | 10.74 | 20.40 |
| 1,3 BUTADIENE | 0.00 | 0.01 | 0.00 | 0.01 | 0.07 | 0.01 | 0.08 | 0.01 |
| HEAVIES (C5+) | 0.17 | 8.80 | 0.17 | 3.94 | 0.18 | 3.04 | 0.17 | 1.39 |

EXAMPLE 7

| COMPONENTS | CATALYST: HYDROGEN FERRIERITE<br>CATALYST CHARGE: 97.70 grams<br>PRESSURE: 17 psia<br>INLET TEMPERATURE: 400° C.<br>WHSV: 14 | | | | | | | |
|---|---|---|---|---|---|---|---|---|
| | INITIAL FEED wt % | INITIAL EFFLUENT wt % | FEED @ 12 HOURS wt % | EFFLUENT @ 12 HOURS wt % | FEED @ 24 HOURS wt % | EFFLUENT @ 24 HOURS wt % | FEED @ 48 HOURS wt % | EFFLUENT @ 48 HOURS wt % |
| METHANE | 0.00 | 0.07 | 0.00 | 0.01 | 0.01 | 0.02 | 0.01 | 0.01 |
| ETHANE | 0.00 | 0.05 | 0.00 | 0.00 | 0.00 | 0.00 | 0.00 | 0.00 |
| ETHYLENE | 0.01 | 0.26 | 0.01 | 0.02 | 0.00 | 0.01 | 0.00 | 0.00 |
| PROPANE | 0.00 | 0.27 | 0.00 | 0.02 | 0.00 | 0.01 | 0.00 | 0.00 |
| CYCLO PROPANE | 0.00 | 0.00 | 0.00 | 0.00 | 0.00 | 0.00 | 0.00 | 0.00 |
| PROPYLENE | 0.00 | 2.51 | 0.00 | 0.53 | 0.00 | 0.48 | 0.00 | 0.27 |
| ISO-BUTANE | 3.41 | 3.84 | 3.41 | 2.77 | 3.49 | 3.34 | 3.38 | 3.31 |
| N-BUTANE | 21.81 | 23.88 | 21.81 | 20.55 | 22.00 | 22.45 | 22.15 | 22.52 |
| METHYL CYC-PROPANE | 0.00 | 0.00 | 0.00 | 0.00 | 0.00 | 0.00 | 0.00 | 0.00 |
| TRANS 2-BUTENE | 17.68 | 15.47 | 17.68 | 18.08 | 17.47 | 22.66 | 17.24 | 26.06 |
| BUTENE-1 | 43.69 | 7.56 | 43.69 | 8.43 | 43.87 | 10.45 | 43.83 | 12.12 |
| ISOBUTYLENE | 0.41 | 27.92 | 0.41 | 20.21 | 0.35 | 20.23 | 0.44 | 14.95 |
| CIS 2-BUTENE | 12.67 | 10.84 | 12.67 | 12.92 | 12.51 | 15.93 | 12.67 | 18.22 |
| 1,3 BUTADIENE | 0.02 | 0.00 | 0.02 | 0.00 | 0.01 | 0.00 | 0.02 | 0.00 |
| HEAVIES (C5+) | 0.29 | 7.31 | 0.29 | 17.39 | 0.29 | 4.42 | 0.27 | 2.54 |

EXAMPLE 8

CATALYST: HYDROGEN FERRIERITE
CATALYST CHARGE: 97.70 grams
PRESSURE: 17–22 psia
INLET TEMPERATURE: 410° C.
WHSV: 14

| COMPONENTS | INITIAL FEED wt % | INITIAL EFFLUENT wt % | FEED @ 12 HOURS wt % | EFFLUENT @ 12 HOURS wt % | FEED @ 24 HOURS wt % | EFFLUENT @ 24 HOURS wt % | FEED @ 48 HOURS wt % | EFFLUENT @ 48 HOURS wt % |
|---|---|---|---|---|---|---|---|---|
| METHANE | 0.11 | 0.08 | 0.08 | 0.05 | 0.08 | 0.02 | 0.05 | 0.02 |
| ETHANE | 0.00 | 0.01 | 0.00 | 0.00 | 0.00 | 0.00 | 0.00 | 0.00 |
| ETHYLENE | 0.00 | 0.04 | 0.00 | 0.02 | 0.00 | 0.01 | 0.00 | 0.01 |
| PROPANE | 0.00 | 0.03 | 0.00 | 0.01 | 0.00 | 0.00 | 0.00 | 0.00 |
| CYCLO PROPANE | 0.00 | 0.00 | 0.00 | 0.00 | 0.00 | 0.00 | 0.00 | 0.00 |
| PROPYLENE | 0.00 | 0.82 | 0.00 | 0.46 | 0.00 | 0.26 | 0.00 | 0.18 |
| ISO-BUTANE | 3.24 | 3.25 | 3.47 | 3.42 | 3.50 | 3.35 | 3.29 | 3.21 |
| N-BUTANE | 29.63 | 30.09 | 23.69 | 24.46 | 23.71 | 24.25 | 22.97 | 23.40 |
| METHYL CYC-PROPANE | 0.00 | 0.00 | 0.00 | 0.00 | 0.00 | 0.00 | 0.00 | 0.00 |
| TRANS 2-BUTENE | 27.38 | 16.59 | 22.30 | 20.70 | 22.29 | 23.27 | 23.57 | 25.12 |
| BUTENE-1 | 19.39 | 9.53 | 33.49 | 12.06 | 33.46 | 13.56 | 30.83 | 13.58 |
| ISOBUTYLENE | 0.19 | 21.81 | 0.27 | 21.20 | 0.27 | 16.72 | 0.36 | 15.16 |
| CIS 2-BUTENE | 19.84 | 12.12 | 16.48 | 15.10 | 16.50 | 16.98 | 18.73 | 17.98 |
| 1,3 BUTADIENE | 0.00 | 0.01 | 0.00 | 0.01 | 0.00 | 0.01 | 0.00 | 0.01 |
| HEAVIES (C5+) | 0.22 | 5.62 | 0.22 | 2.51 | 0.20 | 1.57 | 0.22 | 1.35 |

EXAMPLE 9

CATALYST: HYDROGEN FERRIERITE
CATALYST CHARGE: 97.70 grams
PRESSURE: 24–25 psia
INLET TEMPERATURE: 425° C.
WHSV: 14

| COMPONENTS | INITIAL FEED wt % | INITIAL EFFLUENT wt % | FEED @ 12 HOURS wt % | EFFLUENT @ 12 HOURS wt % | FEED @ 24 HOURS wt % | EFFLUENT @ 24 HOURS wt % | FEED @ 48 HOURS wt % | EFFLUENT @ 48 HOURS wt % |
|---|---|---|---|---|---|---|---|---|
| METHANE | 0.02 | 0.04 | 0.00 | 0.03 | 0.02 | 0.02 | 0.03 | 0.02 |
| ETHANE | 0.00 | 0.01 | 0.00 | 0.00 | 0.00 | 0.00 | 0.00 | 0.00 |
| ETHYLENE | 0.00 | 0.04 | 0.00 | 0.02 | 0.00 | 0.00 | 0.00 | 0.00 |
| PROPANE | 0.00 | 0.02 | 0.00 | 0.00 | 0.00 | 0.00 | 0.00 | 0.00 |
| CYCLO PROPANE | 0.00 | 0.00 | 0.00 | 0.00 | 0.00 | 0.00 | 0.00 | 0.00 |
| PROPYLENE | 0.00 | 0.68 | 0.00 | 0.29 | 0.00 | 0.10 | 0.00 | 0.04 |
| ISO-BUTANE | 3.11 | 3.28 | 3.02 | 3.19 | 3.24 | 3.14 | 3.24 | 3.09 |
| N-BUTANE | 23.09 | 23.63 | 23.17 | 23.37 | 22.95 | 23.01 | 20.35 | 20.34 |
| METHYL CYC-PROPANE | 0.07 | 0.01 | 0.07 | 0.01 | 0.06 | 0.01 | 0.07 | 0.01 |
| TRANS 2-BUTENE | 19.81 | 18.93 | 20.10 | 22.42 | 19.58 | 26.76 | 16.43 | 30.10 |
| BUTENE-1 | 38.65 | 11.80 | 38.12 | 14.04 | 39.25 | 16.81 | 48.28 | 19.22 |
| ISOBUTYLENE | 0.23 | 24.14 | 0.25 | 18.21 | 0.22 | 9.38 | 0.34 | 4.25 |
| CIS 2-BUTENE | 14.84 | 14.15 | 15.06 | 16.70 | 14.49 | 20.01 | 11.02 | 22.64 |
| 1,3 BUTADIENE | 0.00 | 0.01 | 0.01 | 0.01 | 0.00 | 0.01 | 0.05 | 0.02 |
| HEAVIES (C5+) | 0.19 | 3.09 | 0.20 | 1.54 | 0.18 | .56 | 0.18 | .09 |

EXAMPLE 10

CATALYST: HYDROGEN FERRIERITE
CATALYST CHARGE: 97.70 grams
PRESSURE: 17–25 psia
FEED: MTBE processing effluent

| REACTOR INLET TEMP | WHSV | INITIAL | @ 12 HOURS | @ 24 HOURS | @ 48 HOURS | @ 72 HOURS | @ 84 HOURS | @ 96 HOURS | @ 120 HOURS |
|---|---|---|---|---|---|---|---|---|---|
| | | ISOBUTYLENE YIELD (grams isobutylene formed per grams normal butenes in feed) | | | | | | | |
| 390° C. | 14 | 29.17 | 24.91 | 20.60 | 13.84 | | | | |
| 400° C. | 14 | 37.50 | 29.10 | 27.26 | 20.16 | | | | |

-continued

| | | | CATALYST: HYDROGEN FERRIERITE | | | | | |
|---|---|---|---|---|---|---|---|---|
| | | | CATALYST CHARGE: 97.70 grams | | | | | |
| | | | PRESSURE: 17–25 psia | | | | | |
| | | | FEED: MTBE processing effluent | | | | | |
| REACTOR INLET TEMP | WHSV | INITIAL | @ 12 HOURS | @ 24 HOURS | @ 48 HOURS | @ 72 HOURS | @ 84 HOURS | @ 96 HOURS | @ 120 HOURS |
| 410° C. | 14 | 26.25 | 27.97 | 23.06 | 20.63 | | | | |
| 425° C. | 14 | 32.83 | 24.77 | 12.76 | 5.59 | | | | |
| 400° C. | 7 | 18.37* | 14.73 | 11.51 | 8.89 | | | | |
| 425° C. | 7 | 30.87** | 28.76 | 23.36 | 19.04 | 16.69 | 16.03 | 14.64 | 12.81 |
| 440° C. | 7 | 35.77 | 33.79 | 29.42 | 19.78 | 13.35 | 11.03 | | |
| | | | % SELECTIVITY | | | | | | |
| | | (grams isobutylene formed per grams normal butenes consumed) | | | | | | | |
| 390° C. | 14 | 69.46 | 80.23 | 82.79 | 87.75 | | | | |
| 400° C. | 14 | 68.48 | 61.89 | 80.12 | 83.74 | | | | |
| 410° C. | 14 | 76.20 | 86.83 | 89.34 | 89.37 | | | | |
| 425° C. | 14 | 84.13 | 89.24 | 94.16 | 103.76 | | | | |
| 400° C. | 7 | 52.46* | 66.10 | 70.88 | 66.12 | | | | |
| 425° C. | 7 | 72.64** | 85.97 | 86.95 | 90.19 | 89.05 | 90.46 | 96.86 | 95.00 |
| 440° C. | 7 | 71.47 | 91.61 | 95.06 | 97.86 | 99.00 | 99.83 | | |

*1.7 HOURS
**2.47 HOURS

EXAMPLE 11

CATALYST: HYDROGEN FERRIERITE
CATALYST CHARGE: 97.88 grams
PRESSURE: 17–18 psia
INLET TEMPERATURE: 425° C.
WHSV: 7

| COMPONENTS | FEED @ 2.5 HOURS wt % | EFFLUENT @ 2.5 HOURS wt % | FEED @ 12 HOURS wt % | EFFLUENT @ 12 HOURS wt % | FEED @ 24 HOURS wt % | EFFLUENT @ 24 HOURS wt % | FEED @ 48 HOURS wt % | EFFLUENT @ 48 HOURS wt % |
|---|---|---|---|---|---|---|---|---|
| METHANE | 0.07 | 0.05 | 0.07 | 0.03 | 0.03 | 0.03 | 0.05 | 0.01 |
| ETHANE | 0.00 | 0.01 | 0.00 | 0.02 | 0.00 | 0.01 | 0.00 | 0.01 |
| ETHYLENE | 0.00 | 0.04 | 0.00 | 0.00 | 0.00 | 0.00 | 0.00 | 0.00 |
| PROPANE | 0.00 | 0.04 | 0.00 | 0.01 | 0.00 | 0.00 | 0.00 | 0.00 |
| CYCLO PROPANE | 0.00 | 0.00 | 0.00 | 0.00 | 0.00 | 0.00 | 0.00 | 0.00 |
| PROPYLENE | 0.00 | 0.75 | 0.00 | 0.34 | 0.00 | 0.23 | 0.00 | 0.16 |
| ISO-BUTANE | 2.99 | 2.87 | 2.99 | 2.91 | 2.94 | 2.92 | 3.11 | 3.00 |
| N-BUTANE | 21.43 | 21.42 | 21.43 | 21.89 | 21.46 | 21.80 | 22.06 | 22.39 |
| METHYL CYC-PROPANE | 0.06 | 0.00 | 0.06 | 0.00 | 0.06 | 0.00 | 0.07 | 0.00 |
| TRANS 2-BUTENE | 24.41 | 19.71 | 24.41 | 22.78 | 24.55 | 25.15 | 25.14 | 26.92 |
| BUTENE-1 | 32.61 | 9.53 | 32.61 | 11.09 | 32.31 | 12.07 | 30.25 | 12.88 |
| ISOBUTYLENE | 0.33 | 23.47 | 0.33 | 21.89 | 0.35 | 17.87 | 0.25 | 14.40 |
| CIS 2-BUTENE | 17.94 | 13.86 | 17.94 | 16.01 | 18.13 | 17.62 | 19.00 | 18.80 |
| 1,3 BUTADIENE | 0.00 | 0.00 | 0.00 | 0.00 | 0.00 | 0.00 | 0.00 | 0.00 |
| HEAVIES (C5+) | 0.16 | 8.25 | 0.16 | 3.03 | 0.17 | 2.30 | 0.07 | 1.44 |

| COMPONENTS | FEED @ 72 HOURS wt % | EFFLUENT @ 72 HOURS wt % | FEED @ 96 HOURS wt % | EFFLUENT @ 96 HOURS wt % | FEED @ 120 HOURS wt % | EFFLUENT @ 120 HOURS wt % |
|---|---|---|---|---|---|---|
| METHANE | 0.02 | 0.01 | 0.02 | 0.00 | 0.02 | 0.01 |
| ETHANE | 0.00 | 0.00 | 0.00 | 0.00 | 0.00 | 0.00 |
| ETHYLENE | 0.00 | 0.00 | 0.00 | 0.00 | 0.00 | 0.00 |
| PROPANE | 0.00 | 0.00 | 0.00 | 0.00 | 0.00 | 0.00 |
| CYCLO PROPANE | 0.00 | 0.00 | 0.00 | 0.00 | 0.00 | 0.00 |
| PROPYLENE | 0.00 | 0.14 | 0.00 | 0.11 | 0.00 | 0.10 |
| ISO-BUTANE | 3.29 | 3.19 | 3.26 | 3.21 | 3.27 | 3.18 |
| N-BUTANE | 18.36 | 18.71 | 18.56 | 18.99 | 18.59 | 18.85 |
| METHYL CYC-PROPANE | 0.07 | 0.00 | 0.07 | 0.00 | 0.07 | 0.00 |
| TRANS 2-BUTENE | 18.19 | 29.04 | 18.48 | 30.37 | 18.68 | 30.74 |
| BUTENE-1 | 47.41 | 13.95 | 46.61 | 14.58 | 46.34 | 14.86 |
| ISOBUTYLENE | 0.24 | 13.24 | 0.25 | 11.62 | 0.24 | 10.19 |
| CIS 2-BUTENE | 12.28 | 20.30 | 12.60 | 21.01 | 12.63 | 21.59 |

-continued

|  |  |  |  |  |  |  |
|---|---|---|---|---|---|---|
| CATALYST: HYDROGEN FERRIERITE | | | | | | |
| CATALYST CHARGE: 97.88 grams | | | | | | |
| PRESSURE: 17–18 psia | | | | | | |
| INLET TEMPERATURE: 425° C. | | | | | | |
| WHSV: 7 | | | | | | |
| 1,3 BUTADIENE | 0.00 | 0.00 | 0.01 | 0.00 | 0.01 | 0.01 |
| HEAVIES (C5+) | 0.14 | 1.41 | 0.14 | 0.11 | 0.15 | 0.47 |

EXAMPLE 12

| | | | | | | |
|---|---|---|---|---|---|---|
| CATALYST: HYDROGEN FERRIERITE | | | | | | |
| CATALYST CHARGE: 97.70 grams | | | | | | |
| PRESSURE: 16 psia | | | | | | |
| INLET TEMPERATURE: 440° C. | | | | | | |
| WHSV: 7 | | | | | | |

| COMPONENTS | FEED @ INITIAL wt % | EFFLUENT @ INITIAL wt % | FEED @ 12 HOURS wt % | EFFLUENT @ 12 HOURS wt % | FEED @ 24 HOURS wt % | EFFLUENT @ 24 HOURS wt % |
|---|---|---|---|---|---|---|
| METHANE | 0.07 | 0.08 | 0.07 | 0.04 | 0.10 | 0.05 |
| ETHANE | 0.00 | 0.04 | 0.00 | 0.01 | 0.00 | 0.00 |
| ETHYLENE | 0.00 | 0.26 | 0.00 | 0.04 | 0.00 | 0.03 |
| PROPANE | 0.00 | 0.17 | 0.00 | 0.00 | 0.00 | 0.00 |
| CYCLO PROPANE | 0.00 | 0.00 | 0.00 | 0.00 | 0.00 | 0.00 |
| PROPYLENE | 0.00 | 1.66 | 0.00 | 0.36 | 0.00 | 0.23 |
| ISO-BUTANE | 3.44 | 3.29 | 3.44 | 3.38 | 3.39 | 3.26 |
| N-BUTANE | 20.73 | 20.94 | 20.73 | 20.96 | 21.02 | 21.25 |
| METHYL CYC-PROPANE | 0.06 | 0.00 | 0.06 | 0.00 | 0.06 | 0.00 |
| TRANS 2-BUTENE | 21.76 | 16.22 | 21.76 | 19.86 | 22.82 | 21.71 |
| BUTENE-1 | 37.78 | 9.50 | 37.78 | 12.85 | 35.21 | 13.94 |
| ISOBUTYLENE | 0.25 | 27.20 | 0.25 | 25.70 | 0.25 | 22.34 |
| CIS 2-BUTENE | 15.80 | 11.92 | 15.80 | 14.84 | 17.04 | 16.18 |
| 1,3 BUTADIENE | 0.00 | 0.01 | 0.00 | 0.02 | 0.00 | 0.02 |
| HEAVIES (C5+) | 0.11 | 8.71 | 0.11 | 1.94 | 0.11 | 0.99 |

| COMPONENTS | FEED @ 48 HOURS wt % | EFFLUENT @ 48 HOURS wt % | FEED @ 72 HOURS wt % | EFFLUENT @ 72 HOURS wt % | FEED @ 92 HOURS wt % | EFFLUENT @ 92 HOURS wt % |
|---|---|---|---|---|---|---|
| METHANE | 0.06 | 0.01 | 0.02 | 0.02 | 0.08 | 0.06 |
| ETHANE | 0.00 | 0.00 | 0.00 | 0.00 | 0.01 | 0.01 |
| ETHYLENE | 0.00 | 0.02 | 0.00 | 0.01 | 0.00 | 0.01 |
| PROPANE | 0.00 | 0.00 | 0.00 | 0.00 | 0.00 | 0.00 |
| CYCLO PROPANE | 0.00 | 0.00 | 0.00 | 0.00 | 0.00 | 0.00 |
| PROPYLENE | 0.00 | 0.12 | 0.00 | 0.07 | 0.00 | 0.04 |
| ISO-BUTANE | 3.37 | 3.21 | 3.43 | 3.29 | 3.33 | 3.22 |
| N-BUTANE | 20.71 | 20.87 | 20.13 | 20.22 | 22.14 | 22.18 |
| METHYL CYC-PROPANE | 0.07 | 0.00 | 0.07 | 0.00 | 0.07 | 0.00 |
| TRANS 2-BUTENE | 22.29 | 25.18 | 20.13 | 27.47 | 17.63 | 27.38 |
| BUTENE-1 | 36.62 | 16.22 | 41.86 | 17.79 | 42.58 | 18.34 |
| ISOBUTYLENE | 0.25 | 15.17 | 0.25 | 10.40 | 0.44 | 7.83 |
| CIS 2-BUTENE | 16.52 | 18.78 | 14.01 | 20.48 | 13.51 | 20.60 |
| 1,3 BUTADIENE | 0.00 | 0.04 | 0.00 | 0.06 | 0.00 | 0.07 |
| HEAVIES (C5+) | 0.11 | 0.38 | 0.10 | 0.19 | 0.21 | 0.26 |

Figure 2:
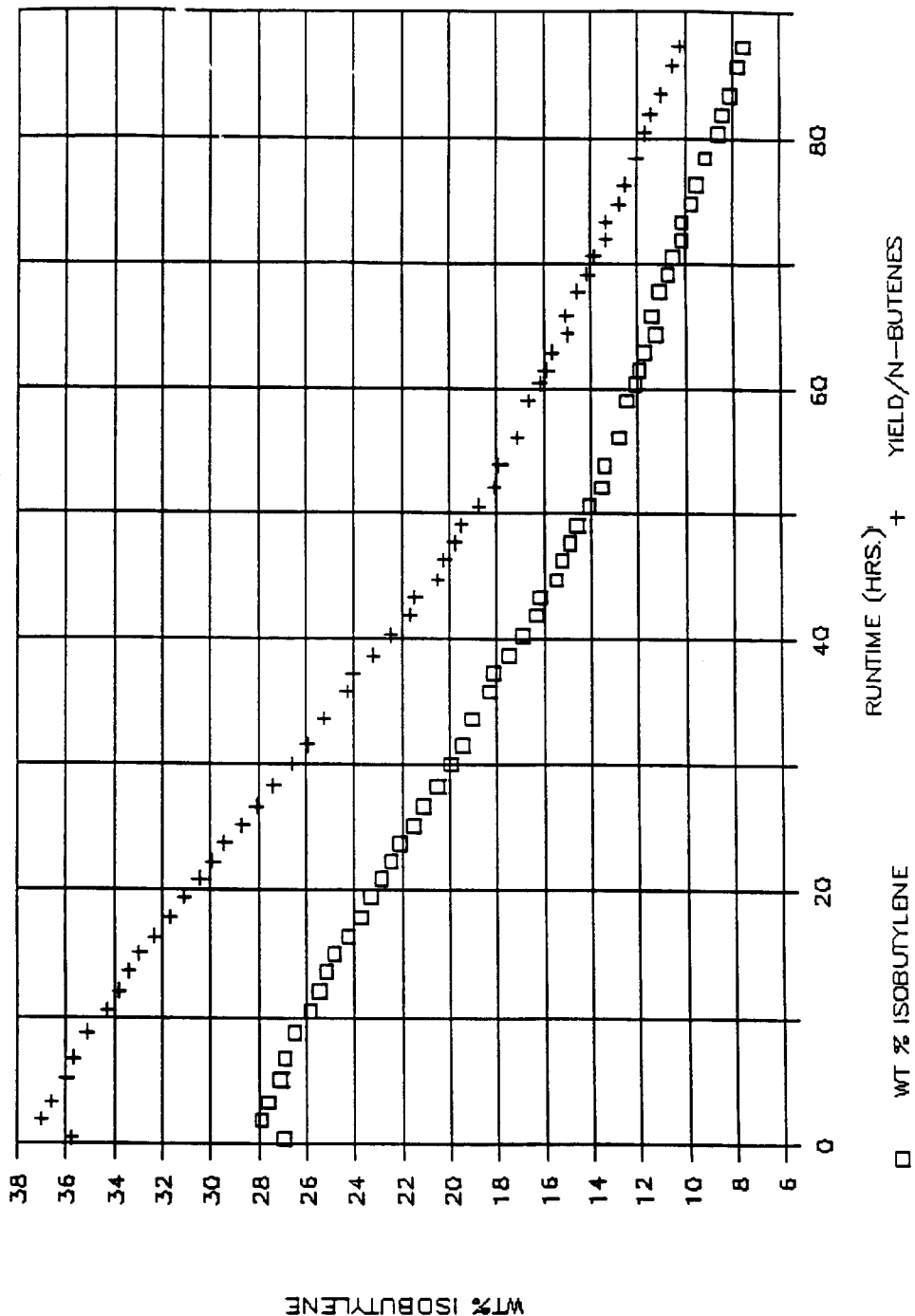
FIG. 2 is a graph of isobutylene yield versus run time illustrative of a process of this invention.

FIG. 1 is a graph of the conversion and selectivity wt % versus run time depicting the results of this example. FIG. 2 is a graph of isobutylene yield and isobutylene wt % versus run time for the results of this example.

EXAMPLE 13

CATALYST: SAPO-11 (Provided by Union Carbide Corporation)
CATALYST CHARGE: 400 grams
INLET TEMPERATURE: 300° C.
PRESSURE: 17–20 psia
WHSV: 1–2

| COMPONENTS | FEED wt % | EFFLUENT @ 1.5 HOURS wt % | EFFLUENT @ 4.7 HOURS wt % | EFFLUENT @ 16.0 HOURS wt % |
|---|---|---|---|---|
| METHANE | 0.00 | 0.01 | 0.00 | 0.00 |
| ETHANE | 0.00 | 0.01 | 0.00 | 0.00 |
| ETHYLENE | 0.00 | 0.08 | 0.03 | 0.01 |
| PROPANE | 0.00 | 0.31 | 0.08 | 0.01 |
| CYCLO PROPANE | 0.00 | 0.00 | 0.00 | 0.00 |
| PROPYLENE | 0.00 | 2.14 | 1.66 | 0.35 |
| ISO-BUTANE | 2.61 | 3.66 | 2.15 | 2.93 |
| N-BUTANE | 26.28 | 17.34 | 15.78 | 20.83 |
| METHYL CYC-PROPANE | 0.06 | 0.00 | 0.00 | 0.00 |
| TRANS 2-BUTANE | 13.61 | 3.32 | 8.01 | 20.84 |
| BUTANE-1 | 48.67 | 1.44 | 3.62 | 10.23 |
| ISOBUTYLENE | 0.42 | 6.05 | 10.12 | 5.93 |
| CIS 2-BUTENE | 6.90 | 2.29 | 5.71 | 14.88 |
| 1,3 BUTADIENE | 1.26 | 0.00 | 0.00 | 0.06 |
| HEAVIES (C5+) | 0.18 | 63.35 | 52.85 | 23.92 |

EXAMPLE 14

CATALYST: SAPO-11 (REGENERATED)*
CATALYST CHARGE: 97.70 grams
PRESSURE: 27 psia
WHSV: 15

| COMPONENTS | FEED wt % | EFFLUENT @ 400° C. & 4 HOURS wt % | EFFLUENT @ 410° C. & 13 HOURS wt % |
|---|---|---|---|
| METHANE | 0.00 | 0.01 | 0.00 |
| ETHANE | 0.01 | 0.01 | 0.01 |
| ETHYLENE | 0.86 | 0.80 | 0.92 |
| PROPANE | 0.00 | 0.00 | 0.00 |
| CYCLO PROPANE | 0.00 | 0.00 | 0.00 |
| PROPYLENE | 0.12 | 2.07 | 0.81 |
| ISO-BUTANE | 0.00 | 0.19 | 0.08 |
| N-BUTANE | 0.04 | 0.94 | 0.70 |
| METHYL CYC-PROPANE | 0.00 | 0.00 | 0.00 |
| TRANS 2-BUTENE | 57.88 | 30.26 | 36.47 |
| BUTENE-1 | 10.74 | 16.51 | 19.31 |
| ISOBUTYLENE | 0.00 | 15.85 | 11.10 |
| CIS 2-BUTENE | 30.26 | 21.79 | 26.61 |
| 1,3 BUTADIENE | 0.01 | 0.13 | 0.16 |
| HEAVIES (C5+) | 0.08 | 11.44 | 3.83 |

* The SAPO-11 catalyst was regenerated by heating it to 500° C. in a muffle furnace.

Examples 15–17 show experimental results using the larger pore hydrogen mordenite. In comparison, Examples 18 and 19 show experimental results reflecting improved results using the smaller pore magnesium mordenite.

EXAMPLE 15

CATALYST: HYDROGEN MORDENITE
CATALYST CHARGE: 97.70 grams
PRESSURE: 22–26 psia
WHSV: 15

| COMPONENTS | FEED wt % | EFFLUENT @ 0.3 HOURS & 327° C. wt % | EFFLUENT @ 2.6 HOURS & 347° C. wt % |
|---|---|---|---|
| METHANE | 0.00 | 0.00 | 0.01 |
| ETHANE | 0.01 | 0.02 | 0.02 |
| ETHYLENE | 0.86 | 0.76 | 1.11 |
| PROPANE | 0.00 | 0.09 | 0.03 |
| CYCLO PROPANE | 0.00 | 0.00 | 0.00 |
| PROPYLENE | 0.12 | 1.97 | 1.79 |
| ISO-BUTANE | 0.00 | 0.35 | 0.19 |
| N-BUTANE | 0.04 | 1.04 | 1.10 |
| METHYL CYC-PROPANE | 0.00 | 0.00 | 0.00 |
| TRANS 2-BUTENE | 57.88 | 25.20 | 32.40 |
| BUTENE-1 | 10.74 | 14.39 | 18.12 |
| ISOBUTYLENE | 0.00 | 2.51 | 1.17 |
| CIS 2-BUTENE | 30.26 | 18.12 | 23.60 |
| 1,3 BUTADIENE | 0.01 | 0.00 | 0.00 |
| HEAVIES (C5+) | 0.08 | 35.56 | 20.48 |

EXAMPLE 16

CATALYST: HYDROGEN MORDENITE
CATALYST CHARGE: 97.70 grams
PRESSURE: 17–19 psia
WHSV: 14

| COMPONENTS | FEED wt % | @3 HOURS & 400° C. wt % | @5 HOURS & 405° C. wt % | @7 HOURS & 423° C. wt % | @8.6 HOURS & 419° C. wt % |
|---|---|---|---|---|---|
| METHANE | 0.04 | 0.03 | 0.03 | 0.03 | 0.03 |
| ETHANE | 0.00 | 0.00 | 0.00 | 0.00 | 0.00 |
| ETHYLENE | 0.00 | 0.01 | 0.00 | 0.00 | 0.00 |
| PROPANE | 0.00 | 0.00 | 0.00 | 0.00 | 0.00 |
| CYCLO PROPANE | 0.00 | 0.00 | 0.00 | 0.00 | 0.00 |
| PROPYLENE | 0.00 | 0.41 | 0.30 | 0.26 | 0.23 |
| ISO-BUTANE | 3.29 | 3.24 | 3.26 | 3.24 | 3.25 |
| N-BUTANE | 21.09 | 21.04 | 21.02 | 21.02 | 21.04 |
| METHYL CYC-PROPANE | 0.06 | 0.00 | 0.00 | 0.00 | 0.00 |
| TRANS 2-BUTENE | 23.64 | 30.91 | 31.56 | 31.41 | 31.64 |
| BUTENE-1 | 34.13 | 17.48 | 17.22 | 17.77 | 17.74 |
| ISOBUTYLENE | 0.25 | 1.57 | 1.28 | 1.28 | 1.15 |
| CIS 2-BUTENE | 17.39 | 22.44 | 22.68 | 22.77 | 22.86 |
| 1,3 BUTADIENE | 0.00 | 0.01 | 0.01 | 0.01 | 0.01 |
| HEAVIES (C5+) | 0.10 | 2.87 | 2.65 | 2.22 | 2.05 |

EXAMPLE 17

CATALYST: M-8 HYDROGEN MORDENITE
CATALYST CHARGE: 97.70 grams
PRESSURE: 23–29 psia
WHSV: 15

| COMPONENTS | FEED wt % | EFFLUENT @ 0.1 HOURS & 317° C. wt % | EFFLUENT @ 5.0 HOURS & 224° C. wt % |
|---|---|---|---|
| METHANE | 0.00 | 0.00 | 0.00 |
| ETHANE | 0.01 | 0.02 | 0.01 |
| ETHYLENE | 0.86 | 0.82 | 0.76 |
| PROPANE | 0.00 | 0.19 | 0.02 |
| CYCLO PROPANE | 0.00 | 0.00 | 0.00 |
| PROPYLENE | 0.12 | 1.33 | 1.30 |
| ISO-BUTANE | 0.00 | 0.46 | 0.15 |
| N-BUTANE | 0.04 | 1.12 | 0.75 |
| METHYL CYC-PROPANE | 0.00 | 0.00 | 0.00 |
| TRANS 2-BUTENE | 57.88 | 30.06 | 32.86 |
| BUTENE-1 | 10.74 | 14.28 | 18.95 |
| ISOBUTYLENE | 0.00 | 2.22 | 1.05 |
| CIS 2-BUTENE | 30.26 | 21.11 | 23.16 |
| 1,3 BUTADIENE | 0.01 | 0.00 | 0.00 |
| HEAVIES (C5+) | 0.08 | 28.38 | 20.99 |

EXAMPLE 18

CATALYST: MAGNESIUM-MORDENITE
CATALYST CHARGE: 96 grams
PRESSURE: 26–32 psia
INLET TEMPERATURE: 320° C.
WHSV: 15

| COMPONENTS | FEED wt % | EFFLUENT @ 0.2 HOURS wt % | EFFLUENT @ 2.0 HOURS wt % |
|---|---|---|---|
| METHANE | 0.00 | 0.00 | 0.01 |
| ETHANE | 0.01 | 0.04 | 0.05 |
| ETHYLENE | 0.86 | 0.44 | 1.08 |
| PROPANE | 0.00 | 0.00 | 0.00 |
| CYCLO PROPANE | 0.00 | 0.00 | 0.00 |
| PROPYLENE | 0.12 | 0.% | 2.04 |
| ISO-BUTANE | 0.00 | 0.19 | 0.25 |
| N-BUTANE | 0.04 | 0.67 | 0.85 |
| METHYL CYC-PROPANE | 0.00 | 0.00 | 0.00 |
| TRANS 2-BUTENE | 57.88 | 30.05 | 36.57 |
| BUTENE-1 | 10.74 | 6.25 | 19.97 |
| ISOBUTYLENE | 0.00 | 10.59 | 3.38 |
| CIS 2-BUTENE | 30.26 | 20.87 | 29.71 |
| 1,3 BUTADIENE | 0.01 | 0.00 | 0.00 |
| HEAVIES (C5 +) | 0.08 | 29.94 | 6.09 |

EXAMPLE 19

CATALYST: MAGNESIUM MORDENITE
CATALYST CHARGE: 97.73 grams
PRESSURE: 19–20 psia
INLET TEMPERATURE: 348° C.
WHSV: 15

| COMPONENTS | FEED wt % | EFFLUENT @ 0.2 HOURS | EFFLUENT @ 2.6 HOURS |
|---|---|---|---|
| METHANE | 0.00 | 0.01 | 0.00 |
| ETHANE | 0.01 | 0.02 | 0.01 |
| ETHYLENE | 0.86 | 0.12 | 0.13 |
| PROPANE | 0.00 | 0.00 | 0.00 |
| CYCLO PROPANE | 0.00 | 0.00 | 0.00 |
| PROPYLENE | 0.12 | 2.16 | 1.19 |
| ISO-BUTANE | 0.00 | 0.28 | 0.12 |
| N-BUTANE | 0.04 | 0.79 | 0.69 |
| METHYL CYC-PROPANE | 0.00 | 0.00 | 0.00 |
| TRANS 2-BUTENE | 57.88 | 32.24 | 38.09 |
| BUTENE-1 | 10.74 | 18.79 | 19.54 |
| ISOBUTYLENE | 0.00 | 4.47 | 2.29 |
| CIS 2-BUTENE | 30.26 | 22.52 | 27.25 |
| 1,3 BUTADIENE | 0.01 | 0.00 | 0.00 |
| HEAVIES (C5+) | 0.08 | 18.60 | 10.69 |

Schematic Flow Chart

Figure 3:
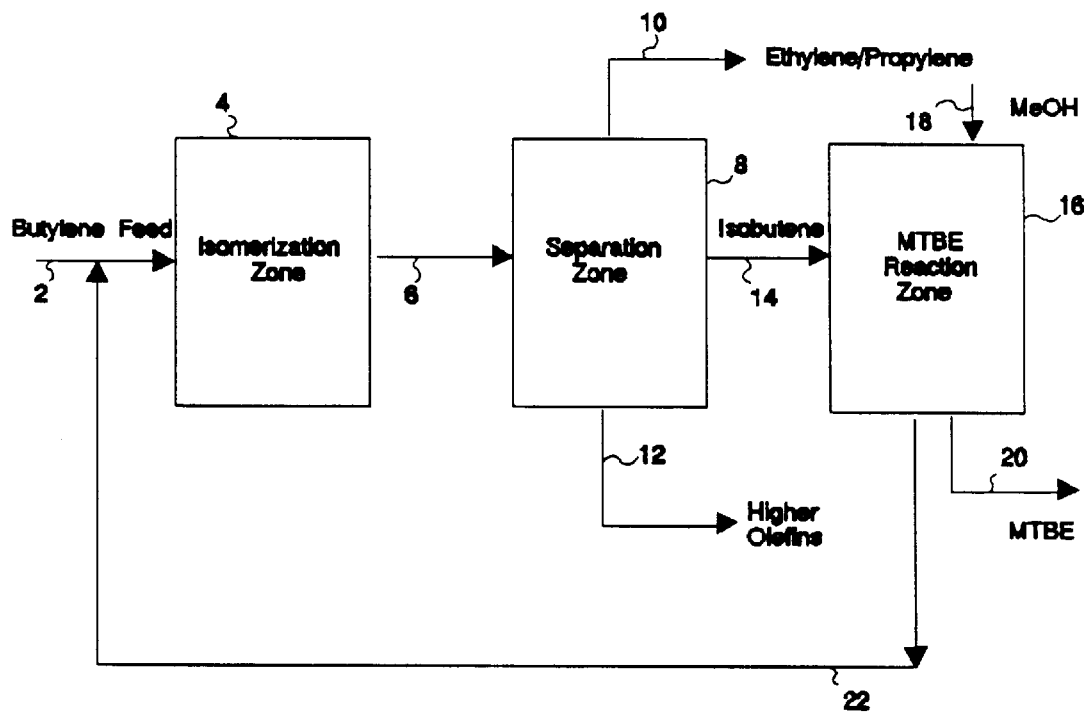
FIG. 3 is a schematic flow scheme of a process of this invention.

FIG. 3 depicts a flow scheme for producing an alkyl-tert-alkyl-ether, particularly methyl-tert-butyl-ether (MTBE) by means of first isomerizing n-butene to isobutylene, separating out an isobutylene stream for further processing to produce MTBE. In the flow scheme, a hydrocarbon stream containing butylene is charged to an isomerization zone 4, via conduit 2. The hydrocarbon stream can be charged continuously. As the butylene feed enters the isomerization zone, it is preferentially vaporized to a gaseous phase. The isomerization zone 4 contains an isomerizing catalyst, preferably the hydrogen form of ferrierite. The isomerization zone is further maintained at isomerizing conditions so as to maximize the structural isomerization of butylene to isobutylene. The effluent from the isomerization zone 4 containing isobutylene is passed through conduit 6 to a separation zone 8. Optionally, the isomerizing catalyst can be regenerated in the isomerization zone 4.

The separation zone 8 is maintained under conditions sufficient to maximize separation of isobutylene from the lighter olefins, ethylene and propylene, and from the heavier olefins, aromatics and paraffins. The separation zone 8 can employ various means known in the art to effect separation of light, medium and heavy olefins, aromatics or paraffins. For example, the zone may comprise a series of adsorbent beds comprising molecular sieves as described in U.S. Pat. Nos. 4,717,784 and 4,210,771, incorporated herein by reference. Or the separation zone may conveniently separate the light, medium and heavy fractions by distillation using processes well known in the art. The lighter olefins, ethylene and propylene, and lighter paraffins are removed via conduit 10. The higher paraffins and olefins, C$_5$ and above, and aromatics are removed via conduit 12. The butylene fraction, comprising isobutylene, is removed from the separation zone via conduit 14 to an MTBE reaction zone 16 containing an etherification catalyst. Thereafter, methanol is fed into the MTBE reaction zone 16 via conduit 18. The MTBE reaction process can be carried out in any one of a number of ways, such as for example taught by U.S. Pat. No. 4,876,394, incorporated herein by reference. The MTBE effluent 20 is recovered preferably as a bottoms product and the unreacted butene/isobutylene stream is recovered and recycled via conduit 22 to the butylene feed at conduit 2.

Additional advantages and modifications will be readily apparent to those skilled in the art. The invention in its broader aspects is therefore not limited to the specific details or representative examples described. Accordingly, departures may be made from the detail without departure from the spirit or scope of the disclosed general inventive concept.

What is claimed is:

1. A method for the highly selective conversion of linear olefins to corresponding isoolefins of the same carbon number which comprises contacting a linear olefin-containing organic feedstock comprising $C_4$ to $C_{10}$ linear olefins with a catalyst comprising a member selected from the group consisting of ZSM-35 and H-ferrierite under skeletal isomerization conditions.

2. The method of claim 1 wherein said conversion is carried out at:
   (a) temperatures between about 250° C. and 650° C.;
   (b) weight hourly space velocities based on hydrocarbons in said feedstock between about 1.0 and about 50 WHSV; and
   (c) linear olefin partial pressures between about 70 and about 140 kPa.

3. The method of claim 1 wherein said conversion:
   (a) is about 12–37 wt. % and
   (b) has a linear olefin to isoolefin selectivity from about 70 wt. % to about 99 wt. %.

4. The method of claim 2 wherein said conversion:
   (a) is at least 11 wt. % and
   (b) has a linear olefin to isoolefin selectivity of at least 80 wt. %.

5. The method of claim 1 wherein said conversion is carried out at:
   (a) temperatures between about 250° and 600° C.;
   (b) weight hourly space velocities based on linear olefin in said feedstock between about 1.0 and 50 WHSV; and
   (c) linear olefin partial pressures between 14 and 140 kPa.

6. The method of claim 5 wherein said conversion:
   (a) is at least 20% wt. % and
   (b) has a linear olefin to isoolefin selectivity of at least 62% wt. %.

7. The method of claim 1 wherein said conversion is carried out at:
   (a) temperatures between about 300° and 475° C.;
   (b) weight hourly space velocities based on hydrocarbons in said feedstock between about 2 and 28 WHSV; and
   (c) linear olefin partial pressures between 70 and 140 kPa.

8. The method of claim 7 wherein said conversion:
   (a) is at least 30 wt. % and
   (b) has a linear olefin to isoolefin selectivity of at least 70 wt. %.

9. The method of claim 1 wherein:
   (a) said linear olefin to isoolefin selectivity is at least 70% at a conversion temperature from 350° C. to 475° C.; and
   (b) said linear olefin partial pressure is above 50 kPa.

10. The method of claim 1 wherein said feedstock comprises $C_4$ to $C_6$ linear olefins.

11. The method of claim 1 wherein said catalyst is reactivated by exposure to a gas comprising oxygen at temperatures of 310°–420° C. for a time sufficient to effect reactivation.

12. The method of claim 1 wherein said catalyst comprises 10.5 to 90 wt. % of a refractory inorganic oxide binder.

13. The method of claim 1 wherein said catalyst comprises 10.5 to 90 wt. % of a silica binder.

14. The method of claim 1 wherein said catalyst comprises 20 wt. % of an alumina binder.

15. The method of claim 1 wherein said organic feedstock comprises at least 40 wt. % n-butenes.

16. The method of claim 1 wherein said organic feedstock comprises cracking process light gas.

17. The method of claim 1 wherein said organic feedstock consists essentially of a $C_4$ hydrocarbon stream.

18. The method of claim 1 wherein said catalyst is ZSM-35.

19. The method of claim 1 wherein said catalyst is H-ferrierite.

20. A method for conversion of linear olefins to corresponding iso-olefins of the same carbon number which comprises contacting a linear olefin-containing organic feedstock comprising $C_4$ to $C_{10}$ linear olefins with a catalyst comprising material having the structure of ZSM-35 under skeletal isomerization conditions, wherein said conversion is carried out at temperatures between about 200° and 650° C., weight hourly space velocities (WHSV) based on linear olefins in said feedstock between 1.0 to about 50 $hr^{-1}$, and linear olefin partial pressures between 70 and 140 kPa, and said catalyst comprises a silica binder.

21. The method of claim 20, wherein said conversion is carried out at temperatures between about 200° and 600° C., weight hourly space velocities (WHSV) based on linear olefins in said feedstock between 1 to 50 $hr^{-1}$ WHSV, linear olefin partial pressures between 70 and 140 kPa, and conversion levels of at least 20 weight percent.

22. The method of claim 20, wherein said conversion is carried out at temperatures between about 200° and 550° C., weight hourly space velocities (WHSV) based on linear olefins in said feedstock between 1 to 50 $hr^{-1}$ WHSV, linear olefin partial pressures between 70 and 140 kPa, and conversion levels of at least 30 weight percent.

23. A method for conversion of linear olefins to corresponding iso-olefins of the same carbon number which comprises contacting under skeletal isomerization conditions a linear olefin-containing organic feedstock comprising $C_4$ to $C_{10}$ linear olefins with a catalyst comprising a) material having the structure of ZSM-35, and b) a silica binder.

24. The method of claim 23 wherein said conversion is carried out at temperatures between about 200 and 650° C., weight hourly space velocities (WHSV) based on linear olefins in said feedstock between 1 to 50 $hr^{-1}$ WHSV, and linear olefin partial pressures between 70 and 140 kPa.

25. The method of claim 23, wherein said conversion is at least 20 weight percent.

26. The method of claim 23 wherein said temperatures are no greater than 440° C.

27. The method of claim 23 wherein said WHSV is no less than about 1.

28. The method of claim 23 wherein said organic feedstock comprises about 40 to 100 wt % n-butene.

29. The method of claim 23 wherein said organic feedstock comprises butylene or amylene.

30. The method of claim 23 wherein said organic feedstock consists essentially of a $C_4$ hydrocarbon stream.

31. The method of claim 23 wherein said organic feedstock consists essentially of a $C_{4+}$ hydrocarbon stream.

32. The method of claim 23 wherein said organic feedstock comprises n-pentenes.

33. A method for conversion of linear olefins to corresponding iso-olefins which comprises
contacting a linear olefin-containing organic feedstock with a catalyst comprising a zeolite having the structure of ZSM-35 under skeletal isomerization conditions, wherein said catalyst comprises 10 to 90.5 wt % of said zeolite and 9.5 to 90 wt % silica binder.

34. The method of claim 33 wherein said conversion is carried out at temperatures between about 250° and 650° C., weight hourly space velocities (WHSV) based on linear olefins in said feedstock of 1 to 30, linear olefin partial pressures between 51 and 1013 kPa, and conversion levels of at least 20 weight percent, and wherein said catalyst comprises 10 to 90.5 wt % of said zeolite and 9.5 to 90 wt % of an inorganic oxide binder.

35. The method of claim 34 wherein said temperatures are between about 250° and 475° C., said weight hourly space velocities (WHSV) are between 2 and 28, said linear olefin partial pressure is between 70 and 140 kPa, and conversion levels are at least 30 weight percent.

36. The method of claim 34 wherein said linear olefin partial pressure is between 70 and 140 kPa.

37. The method of claim 33 wherein said organic feedstock comprises at least 40 wt % n-butenes.

38. The method of claim 33 wherein said feedstock comprises $C_4$ to $C_{10}$ linear olefins.

39. The method of claim 33 wherein said feedstock comprises $C_4$ to $C_6$ linear olefins.

40. The method of claim 33 wherein said organic feedstock consists essentially of a $C_4$ hydrocarbon stream.

41. The method of claim 33 wherein said organic feedstock comprises n-pentenes.

42. The method of claim 34 wherein said temperature is from about 400° C. to 440° C.

43. A method for conversion of linear olefins to corresponding iso-olefins which comprises
contacting a linear olefin-containing organic feedstock with a catalyst comprising a zeolite having the structure of ZSM-35 under skeletal isomerization conditions which comprises linear olefin conversion of at least 20 weight percent, linear olefin partial pressure of greater than 70 kPa and iso-olefin selectivity of greater than 70 wt %,
wherein said catalyst comprises 10 to 90.5 wt % of said zeolite and 9.5 to 90 wt % of an inorganic oxide binder.

44. The method of claim 43 wherein said catalyst comprises 10 wt % of said zeolite.

45. The method of claim 43 wherein said conditions comprise weight hourly space velocities.

46. A method for conversion of linear olefins to corresponding iso-olefins which comprises
contacting a linear olefin-containing organic feedstock with a catalyst comprising a zeolite having the structure of ZSM-35 under skeletal isomerization conditions which comprise weight hourly space velocities (WHSV) based on linear olefins in said feedstock of 1 to 30 wherein said catalyst comprises 10 to 90.5 wt % of said zeolite and 9.5 to 90 wt % of an inorganic oxide binder.

47. A method of converting n-butylenes to isobutylene by a skeletal isomerization reaction wherein said reaction is carried out at a temperature of between 250° C. and 650° C., under a pressure of between 0.5 to 10.0 atmospheres and a space velocity of said n-butylenes of between 1 and 50 Weight Hourly Space Velocity (WHSV) using a catalyst consisting essentially of a zeolite having a pore size structure of at least about 4.2 angstroms and the pore size structure is characterized by intersecting 10-member ring and 8-member ring channels.

48. The method of claim 47, wherein said zeolite is an alumina silicate or an isomorphous substitution T-zeolite in which T is Ga or Fe.

49. The method of claim 47, wherein the ratio of Si/Al is between 5 and 100.

50. The method of claim 47, wherein said zeolite is in the H-form.

51. The method of claim 47, wherein said zeolite possesses a modified pore structure which enhances the shape selectivity of the zeolite.

52. The method of claim 47, wherein said method is carried out under the temperature ranging from about 400° C. to 550° C., the pressure ranges from 0.5 to 10.0 atmospheres, and the space velocity of said n-butylenes ranges from 1.0 to 30 Weight Hourly Space Velocity (WHSV).

53. The method of claim 47, wherein said n-butylenes are a mixture of 1-butylenes, n-butylenes, and MTBE processing hydrocarbon effluent.

54. The method of claim 47, wherein said zeolite is characterized by a topological structure selected from the group consisting of ferrierite, heulandite and stilbite.

55. A process for the skeletal isomerization of an n-olefin of from 4 to 10 carbon atoms to provide a branched olefin product which comprises contacting the n-olefin under skeletal isomerization conditions with, as skeletal isomerization catalyst, an alumina matrix bound zeolite, said zeolite having a pore size of at least about 4.2 angstroms and less than 7.0 angstroms and a pore structure characterized by intersecting 10-member ring and 8-member ring channels.

56. The process of claim 55 wherein the skeletal isomerization conditions include a temperature of between about 200° C. and 550° C., a pressure of between about 0.5 and about 10 atmospheres and a space velocity of n-olefin of between 0.1 and 50 weight hourly space velocity.

57. The process of claim 55 wherein the n-olefin is an n-butene.

58. The process of claim 55 wherein the zeolite is an aluminosilicate or an isomorphously substituted T-zeolite in which T is Ga or Fe.

59. The process of claim 55 wherein the skeletal isomerization conditions include a temperature of between about 250° C. and 475° C., a pressure of between about 0.5 and 10 atmospheres and a space velocity of n-olefin of between about 1.0 and 50 weight hourly space velocity.

60. The process of claim 55 wherein the zeolite is selected from the group consisting of ferrierite, heulandite, stilbite and any combination thereof.

61. A process for the skeletal isomerization of an n-olefin of from 4 to 10 carbon atoms to provide a branched olefin product which comprises contacting the n-olefin under skeletal isomerization conditions with, as skeletal isomerization catalyst, a zeolite present in a binder, said zeolite having a pore size of at least about 4.2 angstroms and a pore structure characterized by intersecting 10-member ring and 8-member ring channels.

62. The process of claim 61 wherein the binder is selected from the group consisting of alumina, silica, silica-alumina, clay, or any combination thereof.

63. The process of claim 61 wherein the skeletal isomerization conditions include a temperature of between 300° C. and 650° C., a pressure of between 0.5 and 10 atmospheres, and a space velocity of n-olefin of between 1 and 50 weight hourly space velocity.

64. The process of claim 61 wherein the n-olefin is an n-butene.

65. The process of claim 61 wherein the zeolite is an aluminosilicate or an isomorphously substituted T-zeolite in which T is Ga or Fe.

66. The process of claim 61 wherein the skeletal isomerization conditions include a temperature of from 400° C. to 550° C., a pressure from 0.5 to 10 atmospheres, and a space velocity of n-olefin of between 1 and 30 weight hourly space velocity.

67. The process of claim 61 wherein the zeolite is selected from the group consisting of ferrierite, heulandite, stilbite, and any combination thereof.

68. A process for the skeletal isomerization of a linear olefin to provide a branched olefin product which comprises contacting a linear olefin under skeletal isomerization conditions with, as skeletal isomerization catalyst, ferrierite which has been acid washed.

69. The process of claim 68 wherein the skeletal isomerization conditions include a temperature of between about 250° C. and 650° C., a pressure of between about 0.5 and about 10 atmospheres and a space velocity of said linear olefin of between about 1.0 and about 50 weight hourly space velocity.

70. The process of claim 68 wherein the linear olefin is contacted with, as skeletal isomerization catalyst, ferrierite which has been acid washed with water and an acid.

71. The process of claim 69 wherein the linear olefin is contacted with, as skeletal isomerization catalyst, ferrierite which has been acid washed with water and nitric or acetic acid.

72. The process of claim 68 wherein the linear olefin is an n-butene and the branched olefin is an isobutene.

* * * * *